(12) United States Patent
Beltramini et al.

(10) Patent No.: US 10,286,385 B2
(45) Date of Patent: May 14, 2019

(54) METHOD FOR PRODUCING A CATALYST

(71) Applicant: BAOSHAN IRON & STEEL CO., LTD., Shanghai (CN)

(72) Inventors: Jorge Beltramini, Brisbane (AU); Muxina Konarova, Brisbane (AU); Fengqiu Tang, Brisbane (AU)

(73) Assignee: BAOSHAN IRON & STEEL CO., LTD., Shanghai (CN)

( * ) Notice: Subject to any disclaimer, the term of this patent is extended or adjusted under 35 U.S.C. 154(b) by 0 days.

(21) Appl. No.: 15/312,424

(22) PCT Filed: May 19, 2015

(86) PCT No.: PCT/CN2015/079243
§ 371 (c)(1),
(2) Date: Nov. 18, 2016

(87) PCT Pub. No.: WO2016/065890
PCT Pub. Date: May 6, 2016

(65) Prior Publication Data
US 2017/0087539 A1     Mar. 30, 2017

(30) Foreign Application Priority Data

May 19, 2014   (AU) ................... 2014901857

(51) Int. Cl.
*B01J 13/00*       (2006.01)
*B01J 27/051*      (2006.01)
(Continued)

(52) U.S. Cl.
CPC ........ *B01J 27/0515* (2013.01); *B01J 23/881* (2013.01); *B01J 23/882* (2013.01);
(Continued)

(58) Field of Classification Search
CPC .. B01J 27/0515; B01J 35/023; B01J 35/1014; B01J 35/1038; B01J 35/1042;
(Continued)

(56) References Cited

U.S. PATENT DOCUMENTS 8,759,596 B2    6/2014  Yie et al.
2005/0059545 A1*  3/2005  Alonso ................. B01J 27/051
                                                          502/220

(Continued)

FOREIGN PATENT DOCUMENTS

CN    10114021 A    2/2007
CN    102616855     8/2012
(Continued)

OTHER PUBLICATIONS

Int'l Search Report for PCT/CN2015/079243, three pages, dated Mar. 7, 2016.
(Continued)

*Primary Examiner* — Patricia L. Hailey
(74) *Attorney, Agent, or Firm* — Nixon & Vanderhye, P.C.

(57)          ABSTRACT

Molybdenum sulphide containing catalysts are provided which have been produced using a microemulsion approach. The catalysts thereby produced have a unique morphology which directly translates into improved performance in the conversion of syngas to alcohol and in the selectivity of this reaction towards producing ethanol.

16 Claims, 11 Drawing Sheets

(51) Int. Cl.
*C07C 29/156* (2006.01)
*B01J 37/03* (2006.01)
*B01J 37/08* (2006.01)
*B01J 37/10* (2006.01)
*B01J 37/18* (2006.01)
*B01J 23/881* (2006.01)
*B01J 23/882* (2006.01)
*B01J 23/883* (2006.01)
*B01J 35/00* (2006.01)
*B01J 35/02* (2006.01)
*B01J 35/10* (2006.01)

(52) U.S. Cl.
CPC ........... *B01J 23/883* (2013.01); *B01J 35/002* (2013.01); *B01J 35/0013* (2013.01); *B01J 35/023* (2013.01); *B01J 35/109* (2013.01); *B01J 35/1014* (2013.01); *B01J 35/1019* (2013.01); *B01J 35/1038* (2013.01); *B01J 35/1042* (2013.01); *B01J 35/1061* (2013.01); *B01J 37/031* (2013.01); *B01J 37/035* (2013.01); *B01J 37/082* (2013.01); *B01J 37/10* (2013.01); *B01J 37/18* (2013.01); *C07C 29/156* (2013.01); *Y02P 20/52* (2015.11)

(58) Field of Classification Search
CPC .... B01J 35/1061; B01J 13/00; B01J 13/0026; C07C 29/156
USPC .............. 502/220–222; 516/220–222, 21–22
See application file for complete search history.

(56) References Cited

U.S. PATENT DOCUMENTS

| | | | |
|---|---|---|---|
| 2005/0065044 A1* | 3/2005 | Migdal | C10M 159/18 508/230 |
| 2007/0161505 A1* | 7/2007 | Pereira-Almao | B01J 27/049 502/216 |
| 2009/0023965 A1* | 1/2009 | Pereira | B01J 23/85 585/250 |
| 2015/0182952 A1* | 7/2015 | Alvarez Contreras | B01J 27/0515 502/220 |

FOREIGN PATENT DOCUMENTS

| | | |
|---|---|---|
| CN | 102989512 | 3/2013 |
| WO | 2007/059621 | 5/2007 |

OTHER PUBLICATIONS

Written Opinion of ISA for PCT/CN2015/079243, five pages, dated Mar. 7, 2016.
Paris, et al., "K—Ni—MoS$_2$ Catalyst Prepared by Microemulsion for Mixed Alcohol Synthesis", Abstract, pp-19, pp. 135-136, CRS-2 Conference, Lund University, Sweden (2013).
Escalona et al., Catalysis Letters 112:3-4, pp. 227-230 (2006).

* cited by examiner (b)

(c)

(a)

(b)

(a)

(b)

METHOD FOR PRODUCING A CATALYST

This application is the U.S. national phase of International Application No. PCT/CN2015/079243, filed 19 May 2015; which designated the U.S. and claims priority to Patent Application No. AU 2014901857, filed 19 May 2014; the entire contents of each of which are hereby incorporated by reference.

FIELD OF THE INVENTION

The invention relates to the field of catalysts. More particularly, this invention relates to a method of producing a catalyst, a catalyst thereby formed and the use thereof in catalysing a chemical reaction.

BACKGROUND TO THE INVENTION

Any reference to background art herein is not to be construed as an admission that such art constitutes common general knowledge in Australia or elsewhere.

The use of catalysts in speeding up the rate of a wide range of chemical reactions or providing access to reaction products that might not otherwise be economically feasible is well known. Particularly useful in an industrial setting is the formation of alcohols, such as ethanol, from syngas which is a mixture of, largely, carbon monoxide (CO) and hydrogen ($H_2$).

Catalysts that are suitable for syngas to alcohol conversion can be categorised as Rh-based, modified Fisher-Tropsch synthesis catalysts, modified methanol synthesis catalysts and $MoS_2$-based catalysts. The $MoS_2$-based catalysts have achieved useful levels of CO conversion with favourable ethanol selectivity.

Variations on the $MoS_2$ catalyst include the $Ni(Co)MoS_2$ catalyst, also known as a hydrotreating catalyst, which is used mainly to remove sulphur, nitrogen and oxygen from crude oil feedstock. Mixed Ni and/or Co $MoS_2$ catalysts have also been used in syngas to ethanol conversion.

Syngas to liquid catalysts are often very expensive to produce due to the involvement of precious metals in their composition as well as the intensive and cyclical approach used for their synthesis. This has limited their industrial use.

To date most work in this technology area has focused on the composition of the catalyst including ratios of dopants and promoter atoms to Mo, and the like along with variations in reaction conditions for the syngas to alcohol transformation, such as varying pressure, syngas ratio, space velocity, and $CO_2$ or $H_2S$ addition into feed gas. There has been little exploration on the importance of the approach to the synthesis of the catalysts themselves and the effects of the synthesis parameters on catalyst properties.

It would be useful to provide a method for producing a catalyst suitable for syngas conversion which is straightforward in operation and which can provide for a catalyst with useful morphology.

OBJECT OF THE INVENTION

It is an aim of this invention to provide a method of producing a catalyst which overcomes or ameliorates one or more of the disadvantages or problems described above, or which at least provides a useful alternative.

Other preferred objects of the present invention will become apparent from the following description.

SUMMARY OF INVENTION

According to a first aspect of the invention there is provided a method of producing a catalyst including the steps of:
(a) providing a non-polar solvent;
(b) forming $MoS_2$ within the non-polar solvent by combining, in aqueous solution added to the non-polar solvent, a sulphide compound and a molybdenum compound; and
(c) adding a salt of a transition metal selected from the group consisting of nickel, cobalt and iron to the non-polar solvent,
to thereby to form a water-in-oil emulsion and produce the catalyst.

Preferably, the non-polar solvent is selected from the group consisting of oils, aliphatic hydrocarbons, saturated cyclic hydrocarbons, aromatic hydrocarbons and halogenated hydrocarbons.

In one embodiment, the non-polar solvent is selected from the group consisting of pentane, hexane, octane, isooctane, decane, dodecane, cyclohexane, methylcyclohexane, dimethylcyclohexane, ethylcyclohexane, cyclopentane, cycloheptane, cyclooctane, toluene, xylenes, ethylbenzene, cumene, benzene, perch loroethylene, tetrachloroethylene, 1,1,1-trich loroethane and carbon tetrachloride.

In one embodiment, the step of forming the $MoS_2$ within the non-polar solvent is achieved by: (i) adding an aqueous solution of the sulphide to the non-polar solvent; and (ii) adding an aqueous solution of the molybdenum compound to the non-polar solvent.

Preferably, the aqueous solution of the molybdenum compound is added to the non-polar solvent containing the aqueous solution of the sulphide.

The sulphide may be any at least partly water-soluble sulphide source including a wide range of sulphide salts and related compounds which can act as a sulphide source.

Suitably, the sulphide is ammonium sulphide or is provided by a thiourea.

In one embodiment, the molybdenum compound is a molybdate, preferably ammonium molybdate tetrahydrate.

In one embodiment, the salt of the transition metal is selected from the group consisting of a nitrate, acetate, halide, sulphate, sulphide, oxalate or carbonate salt.

Preferably, the salt of the transition metal is added to the non-polar solvent as an aqueous solution.

Suitably, the emulsion is a microemulsion.

In one embodiment, the method further includes the step of stirring the water-in-oil emulsion.

In one embodiment, the method further includes the step of collecting the catalyst after it has precipitated in the emulsion.

The method may further include the step of drying and or heating the collected catalyst.

Suitably, the non-polar solvent comprises a surfactant, preferably a non-ionic surfactant.

The non-ionic surfactant may be a polyoxyethenylated surfactant.

In one embodiment, there is provided a method of producing a catalyst including the steps of:
(a) providing an oil phase of a non-polar solvent comprising a non-ionic surfactant;
(b) adding an aqueous solution of a sulphide compound to the non-polar solvent;
(c) adding an aqueous solution of a molybdenum compound to the mixture formed in step (b);

(d) adding an aqueous solution of a salt of a transition metal selected from the group consisting of nickel, cobalt and iron to the non-polar solvent;
(e) allowing an emulsion to form; and
(f) collecting the catalyst as a precipitate,
to thereby produce the catalyst.

The various elements described in detail above apply equally to this particular embodiment.

A second aspect of the invention resides in a catalyst of general formula $TMoS_2$, wherein T represents a transition metal element selected from the group consisting of nickel, cobalt and iron, having a BET surface area of greater than 80 $m^2/g$ and a pore volume of between about 0.3 to about 0.6 ml.

Preferably, the BET surface area is greater than 100 $m^2/g$.

Suitably, the pore volume is between about 0.35 to about 0.5 ml.

A third aspect of the invention resides in a catalyst when produced by the method of the first aspect.

Suitably the catalyst is a catalyst of general formula $TMoS_2$ wherein T represents a transition metal element selected from the group consisting of nickel, cobalt and iron.

According to a fourth aspect of the invention there is provided a method of catalysing a chemical reaction using the catalyst of the second or third aspects.

In one embodiment, the chemical reaction is the conversion of syngas to one or more alcohols.

Preferably, the alcohol is ethanol.

In an alternative embodiment, the chemical reaction is a hydrodesulfurisation reaction.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein.

DETAILED DESCRIPTION OF THE DRAWINGS

Figure 1:
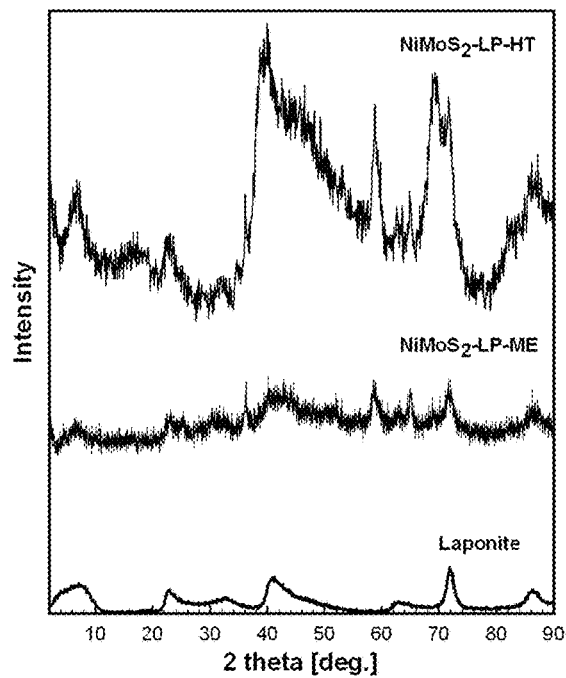
FIG. 1 is a series of X-ray diffraction (XRD) patterns of laponite and laponite with catalysts deposited thereon.

The present invention is predicated, at least in part, on the finding that molybdenum sulphide containing catalysts which have been produced using a microemulsion approach have a unique morphology which directly translates into improved performance in the conversion of syngas to alcohol and in the selectivity of this reaction towards producing ethanol. The present invention shows that the advantageous morphology of the catalyst is a direct result of the synthesis approach and that distinct advantages in performance can be attained by controlling the synthesis appropriately. The invention thus resides in a catalyst with unique catalytic properties and in the method of obtaining same.

In this patent specification, adjectives such as first and second, left and right, front and back, top and bottom, etc., are used solely to define one element or method step from another element or method step without necessarily requiring a specific relative position or sequence that is described by the adjectives.

Unless defined otherwise, all technical and scientific terms used herein have the same meaning as would be commonly understood by those of ordinary skill in the art to which this invention belongs.

As used herein, the term "water-in-oil emulsion" refers to a water-in-oil mixture in which the oil forms a continuous phase and the water is in discontinuous droplets. A water-in-oil emulsion can be distinguished from an oil-in-water emulsion by using an electrical emulsion tester.

The term "oil phase" as used herein in relation to a water-in-oil emulsion refers to all components in the reaction mixture that individually exceed their solubility limit in the water phase; these are materials that generally have solubilities of less than 1% in distilled water, however, water phase components such as salts may decrease the solubility of certain oils resulting in their partitioning into the oil phase. The term explicitly includes hydrophobic or non-polar solvents which may not strictly be defined as "oils" in the classical sense. Typically, the oil phase will be a non-polar solvent, such as cyclohexane.

The term "microemulsion", as used herein, refers to a dispersion made of water, oil and surfactant(s) that is an isotropic and thermodynamically stable system having a dispersed domain diameter varying approximately from 1 to 100 nm, usually from 10 to 50 nm.

In a first aspect of the invention, there is provided a method of producing a catalyst including the steps of:
(a) providing a non-polar solvent;
(b) forming $MoS_2$ within the non-polar solvent by combining, in aqueous solution added to the non-polar solvent, a sulphide compound and a molybdenum compound; and (c) adding a salt of a transition metal selected from the group consisting of nickel, cobalt and iron to the non-polar solvent, to thereby to form a water-in-oil emulsion and produce the catalyst.

Preferably, the non-polar solvent is selected from the group consisting of oils, aliphatic hydrocarbons, saturated cyclic hydrocarbons, aromatic hydrocarbons and halogenated hydrocarbons.

In one embodiment, the non-polar solvent is selected from the group consisting of pentane, hexane, octane, isooctane, decane, dodecane, cyclohexane, methylcyclohexane, dimethylcyclohexane, ethylcyclohexane, cyclopentane, cycloheptane, cyclooctane, toluene, xylenes, ethylbenzene, cumene, benzene, perch loroethylene, tetrachloroethylene, 1, 1, 1-trich loroethane and carbon tetrachloride.

It will be appreciated that the non-polar solvent will be chosen, not only on polarity and therefore its ability to form an emulsion with the aqueous phase, but also on the basis of ease of removal after the catalyst has formed and compatibility with the reagents employed.

In one embodiment, the step of forming the $MoS_2$ within the non-polar solvent is achieved by: (i) adding an aqueous solution of the sulphide to the non-polar solvent; and (ii) adding an aqueous solution of the molybdenum compound to the non-polar solvent.

Preferably, the aqueous solution of the molybdenum compound is added to the non-polar solvent containing the aqueous solution of the sulphide. In this regard it has been found preferable to first add the sulphide, such as ammonium sulphide, to the oil phase followed by the addition of the molybdenum compound as this assists in reducing the formation of undesirably large droplets and instead favours formation of the $MoS_2$ microemulsions in-situ.

The sulphide may be any at least partly water-soluble sulphide source including a wide range of sulphide salts and related compounds which can act as a sulphide source. A variety of sulphide salts which are known to be water soluble are available from commercial sources. Alkali metal sulphides and alkaline-earth metal sulphides may be appropriate.

Suitably, the sulphide is ammonium sulphide or is provided by a thiourea compound.

Any molybdenum-containing compound which is water soluble may be appropriate. The solubility of such compounds can be sourced from standard reference texts or can be ascertained through simple experimentation. Any molybdate compound may be suitable. The molybdenum compound may be selected rom the group consisting of ammonium molydates, molybdenum oxides and water soluble alkali metal and alkaline earth metal molybdates.

In one embodiment, the molybdenum compound is ammonium molybdate tetrahydrate.

Suitably, both the solution of the sulphide and the solution of the molybdenum compound are aqueous solutions. The aqueous solutions contain water as the major solvent but the presence of other solvents and agents to aid in solubilising the substrates is considered within the scope of the term.

Nickel, cobalt and iron have been chosen as the transition metal as the catalyst must be capable of breaking bonds, such as $H_2$ and CO bonds, and these metals have been found to be particularly suitable in this regard.

In one embodiment, the salt of the transition metal is selected from the group consisting of a nitrate, acetate, halide, sulphate, sulphide, oxalate or carbonate salt. Each of these salts may be considered to have been explicitly disclosed in combination with the nickel, cobalt and iron.

Preferably, the transition metal salt is a nickel nitrate, more preferably nickel (II) nitrate hexahydrate.

Preferably, the salt of the transition metal is added to the non-polar solvent as an aqueous solution.

In one embodiment, the microemulsion is formed substantially by the aqueous solution in which one or more of the sulphide, molybdenum compound or transition metal salt is dissolved.

In one embodiment, the method further includes the step of stirring the water-in-oil emulsion. Stirring is useful to ensure the formation of a suitable microemulsion. The stirring may be after addition of the sulphide compound and prior to addition of the molybdenum compound. Preferably, the mixture if stirred after addition of the sulphide compound and after addition of the molybdenum compound to ensure microemulsion formation.

In one embodiment, the method further includes the step of collecting the catalyst after it has precipitated in the emulsion. Upon addition and mixing of the reagents the catalyst will form as a solid and can be easily collected by standard means, such as filtration. Alternatively, the collection may simply be the removal of one or more of the solvents to concentrate or to leave behind only the solid product.

The method may further include the step of drying and or heating the collected catalyst. It is an advantage of the present method that a high temperature treatment step is not required. The drying and heating herein is simply to remove solvent and or surfactant from the final product and it will be appreciated that while higher temperatures can achieve this aim more efficiently they are not strictly required.

Suitably, the non-polar solvent comprises a surfactant, preferably a non-ionic surfactant. The surfactant may assist in stabilising the microemulsions formed during production of the catalyst.

The non-ionic surfactant may be a polyoxyethenylated surfactant.

The method may further include the addition of a dopant. The dopant may be an alkali or alkaline earth metal. Suitably, the dopant may be selected from the group consisting of potassium, caesium and rubidium.

The method may further include the addition of a promoter agent. The promoter agent may be selected from the group consisting of alkaline metals, alkali earth metals, rhodium, ruthenium, palladium, platinum and plutonium. More suitably the promoter agent may be selected from potassium, sodium, ruthenium, palladium and plutonium. The promoter agent may be added before or with the addition of the transition metal salt. The promoter agent may improve the syngas CO conversion efficiency or selectivity for production of an alcohol product.

The production of the catalyst described above will result in an 'unsupported' catalyst. That is, one which is not intimately associated with or adhered to a support scaffold. The use of clays, naturally occurring or synthetic, are common as a support for the molybdenum catalyst.

Therefore, in one embodiment, the method further includes the step of adding a support to the non-polar solvent. Preferably, the support is added after the emulsion has been allowed to form In one embodiment, the support is a clay which may be natural or synthetic. Suitably, the clay is a silicate In one embodiment, the clay may be a phytosilicate.

In one embodiment, the support may be selected from the group consisting of laponite, bentonite, montmorillonite, hectorite and beidellite. Laponite is a preferred support.

In one particular embodiment, there is provided a method of producing a catalyst including the steps of:
(a) providing an oil phase of a non-polar solvent comprising a non-ionic surfactant;
(b) adding an aqueous solution of a sulphide compound to the non-polar solvent;
(c) adding an aqueous solution of a molybdenum compound to the mixture formed in step (b);
(d) adding an aqueous solution of a salt of a transition metal selected from the group consisting of nickel, cobalt and iron to the non-polar solvent;
(e) allowing an emulsion to form; and
(f) collecting the catalyst as a precipitate
to thereby produce the catalyst.

Each of the various elements, both individually and collectively, described in detail above in relation to the first aspect apply equally to this particular embodiment.

A second aspect of the invention resides in a catalyst of general formula $TMoS_2$, wherein T represents a transition metal element selected from the group consisting of nickel, cobalt and iron, having a BET surface area of greater than about 80 $m^2/g$ and a pore volume of between about 0.30 to about 0.60 ml.

Preferably, the BET surface area is greater than about 100 $m^2/g$. In one embodiment, the BET surface area is between about 60 to about 180 $m^2/g$, or about 80 to about 160 $m^2/g$, preferably between about 90 to about 150 $m^2/g$, more preferably between about 100 to about 140 $m^2/g$ and even more preferably between about 110 to about 130 $m^2/g$. The values given here relate to the unsupported catalyst. That is, the catalyst without deposition onto the clay support.

Suitably, the pore volume is between about 0.35 ml to about 0.50 ml, preferably between about 0.40 to about 0.5 ml inclusive of values of about 0.40, 0.41, 0.42, 0.43, 0.44, 0.45, 0.46, 0.47, 0.48 and 0.49 ml.

The average pore size may be between about 2.5 to about 5.0 nm, preferably between about 3.0 to about 4.5 nm, more preferably about 3.3, 3.4, 3.5, 3.6 or 3.7 nm.

The present catalysts display an ideal morphology of fine particles in the region of 10 to 50 nm diameter, preferably 15 to 35 nm, more preferably about 20 nm of the active species which, when deposited onto a silicate support, are homogenously deposited onto said support. The catalyst particles are found to be uniformly distributed on the support.

The present catalysts have highly disordered and short sulphide layers. The short sulphide layers may have a length between 3 nm to about 20 nm, suitably between about 5 nm to about 15 nm, and preferably about 10 nm. The term "about" as used herein means that the number is nominally the value but the actual value may vary from this precise value to an unimportant degree.

Advantageously, the catalyst does not consist of large aggregates. The absence of large aggregates result in a higher surface area, and therefore allows for increased catalytic activity as more hydrotreating reactions can occur in the same period. The catalyst also has highly disordered sulphide layers. These highly disordered sulphide layers are readily reduced in a syngas atmosphere by releasing sulfur from the structure. The release of sulphur from the catalyst structure creates anionic vacancies that promote the formation of alcohol through $CH_3$-methyl and CO coupling. It is postulated that the combination of the highly disordered sulphide layers and the coordinated unsaturated molybdenum sites allow for the efficient formation of alcohol, in particular ethanol, from syngas.

As discussed, the method of producing the catalyst described herein results in catalysts having highly disordered $MoS_2$ layers. The catalysts comprise small, plate-shaped particles.

The catalyst may further comprise a promoter agent. In one embodiment, the promoter agent is selected from the group consisting of alkaline metals, alkali earth metals, rhodium, ruthenium, palladium, platinum and plutonium. More suitably the promoter agent may be selected from potassium, sodium, ruthenium, palladium and plutonium.

The key structural features of the catalyst, discussed above, differentiate the present invention from those of the prior art and directly lead to the improved catalytic performance. The improved catalytic performance arises from, amongst other things, the higher surface area and particularly the advantageously highly disordered structure of the catalyst described herein. A comparison of the present catalyst with the HT catalysts show that the present catalyst consists of significantly smaller particles which do not aggregate to the same degree of those of the HT catalysts. This results in the present catalyst having a larger surface area to perform catalytic reactions, and in turn leads to higher catalytic activity. The highly disordered sulphide layers allow for sulphur release and so increase the availability of vacant catalytic sites.

The catalyst of the second aspect may be supported on a clay support, as already described in detail for the first aspect which disclosure is considered to be reproduced here in full.

A third aspect of the invention resides in a catalyst when produced by the method of the first aspect Suitably the catalyst is a catalyst of general formula $TMoS_2$ wherein T represents a transition metal element selected from the group consisting of nickel, cobalt and iron.

Preferably, the catalyst is selected from the group consisting of a nickel molybdenum sulphide, a cobalt molybdenum sulphide and an iron molybdenum sulphide.

In one embodiment, the catalyst is $NiMoS_2$ which may be supported or unsupported.

The characteristics of the catalysts of the invention described for the first and second aspects are considered to be reproduced here for the purpose of the third aspect and vice versa.

According to a fourth aspect of the invention there is provided a method of catalysing a chemical reaction using the catalyst of the second or third aspects.

In one embodiment, the chemical reaction is selected from the group consisting of the conversion of syngas to an alcohols or a hydrodesulfurisation reaction.

The conversion of syngas may be to methanol and/or ethanol. Preferably, the alcohol is ethanol.

The supported catalyst may have a CO conversion of at least about 10 mol %, preferably at least about 12 mol %. An upper conversion of about 20 mol % may be seen in supported catalysts although this may vary significantly based on the support used and the manner of production. The supported catalyst also has a BET surface area of greater than at least 250 $m^2/g$ and preferably about 300 $m^2/g$.

Even higher CO conversions can be achieved with an unsupported catalyst of the invention where values of greater than about 15, 20, 25 and 30 mol % are observed. Thus, the CO conversion of the unsupported catalyst may be between about 15 to 50 mol %, 20 to 45 mol %, 25 to 40 mol % or 30 to 38 mol %.

The unsupported catalyst of the invention may have a selectivity of at least about 15, 20, or 25 mol % for ethanol. The selectivity for ethanol may be between about 15 to 40 mol %, 20 to 35 mol % or 20 to 30 mol %.

In an alternative embodiment, the chemical reaction is a hydrotreating or related hydrodesulfurisation reaction.

The examples which follow merely show one or more embodiments of the invention to assist with the understanding thereof. They are not to be considered as limiting upon the scope of any of the claims. In the following examples, to better illustrate the advantages in catalyst morphology and hence performance provided by the method of the invention, a comparison is made between a molybdenum catalyst made using a standard hydrothermal method and that same catalyst made using the method of the present invention (described below as the microemulsion method). Each approach is also employed on a support and without a support to thereby demonstrate the effect of the catalyst particles alone and when deposited on a support.

EXPERIMENTAL

Materials and Methods

The crystalline phase of the $NiMoS_2$/Laponite was identified using X-ray diffraction (MiniFlex, Rigaku) analysis with CoKa radiation. The internal morphology of the samples was observed using a high-resolution Transmission Electron Microscope (TEM) (200 kV, JEOL). $N_2$ absorption/desorption isotherms of samples at −196° C. were obtained using a TriStar II Micrometrics Surface Analyzer. XPS data was acquired using a Kratos Axis ULTRA X-ray Photoelectron Spectrometer incorporating a 165 mm hemispherical electron energy analyser. The incident radiation was Monochromatic Al Kα X-rays (1486.6 eV) at 225 W (15 kV, 15 ma). Survey (wide) scans were taken at analyser pass energy of 160 eV and multiplex (narrow) high resolution scans at 20 eV. Survey scans were carried out over a 1200-0 eV binding energy range with 1.0 eV steps and a dwell time of 100 ms. Narrow high-resolution scans were run with 0.05 eV steps and 250 ms dwell time. Base pressure in the analysis chamber was $1.0 \times 10^{-9}$ torr and during sample analysis $1.0 \times 10^{-8}$ torr. Atomic concentrations were calculated using the CasaXPS version 2.3.14 software and a Shirley baseline with Kratos library Relative Sensitivity Factors (RSFs). Peak fitting of the high-resolution data was also carried out using the CasaXPS software. A CHNS elemental analyser (Thermo Electron Corp. Flash EA-1112 Series) was used to determine carbon content.

The catalytic tests were performed at 310° C., 60 bar, GHSV=1044 $h^{-1}$ in a high-pressure fixed bed reactor setup. The stainless-steel fixed bed reactor (i.d. 10 mm; length 100 mm) with a thermocouple positioned inside was inserted in a furnace. The catalyst was reduced under hydrogen atmosphere at 450° C. for 4 hours before the reaction. In all catalytic tests, premixed syngas with a $H_2$/CO ratio of 2/1 and 4% of $N_2$ (internal standard) was used as feed. The mass flow controller (MFC, Bronkhorst High-Tech B.V) regulated the inlet gas flow rate. Gaseous products leaving the reactor passed through the condenser to obtain the liquid fraction of products. The outlet gas stream composition was analysed by gas chromatography equipped with a thermal conductivity detector (Shimadzu GC-2014). Liquid samples were discharged from the condenser every 12 hours and analysed by GC equipped with a flame ionization detector (Shimadzu GC-8A).

Preparation of Laponite Supported $NiMoS_2$—Microemulsion Method

The clay, Laponite RD, supplied by Laporte Industries Ltd, WA USA, was used as a support material. Laponite powder (0.5 g) was dispersed in 50 mL of water. The suspension was stirred until it formed an opaque solution. Meanwhile, the oil phase containing 100 mL cyclohexane and 6 mL non-ionic surfactant (Brij-30, Sigma-Aldrich) was stirred in a beaker at room temperature. Then, 5 mL of sulphur source (ammonium sulphide solution 21 wt. %, Sigma-Aldrich) was added into the oil phase. After several minutes of stirring, 2 mL (25 wt %) aqueous solution of ammonium molybdate tetrahydrate (Sigma-Aldrich, 83.0% $MoO_3$ basis) was added dropwise into the water in oil (w/o) microemulsions.

This procedure was followed by the addition of 1 mL (37.5 wt %) nickel (II) nitrate hexahydrate (Sigma-Aldrich) aqueous solution. The black w/o microemulsion was stirred for an hour to allow sufficient mixing. Laponite (dispersed in 50 mL $H_2O$) was introduced into the w/o microemulsion system. Addition of laponite destabilised w/o microemulsions leading to a deposition of precipitants (Ni, Mo and S) onto the laponite surface. Subsequently, cyclohexane was removed by a rotary evaporator. The black precipitate was further heat-treated under a nitrogen atmosphere at 350° C. for 4 hours to remove the surfactant. The supported catalyst product produced by this microemulsion method is referred to herein as $NiMoS_2$-LP-ME.

Preparation of Unsupported $NiMoS_2$—Microemulsion Method

The experimental procedure given above was followed to afford the unsupported catalyst with the exception of the steps relating to laponite. The unsupported catalyst product produced by this microemulsion method is referred to herein as $NiMoS_2$-ME.

Preparation of Laponite Supported $NiMoS_2$—hydrothermal method $NiMoS_2$-LP catalyst was prepared by hydrothermal synthesis as follows: 5 grams of Laponite was dispersed in 250 mL of water. The suspension was stirred until it formed an opaque solution. 10 mL of surfactant (Tergitol 15-S-9, Sigma-Aldrich) was added to the Laponite solution. The suspension was then stirred for 2 hours to allow sufficient mixing. Meanwhile two aqueous solutions of $(NH_4)_2MoS_4$ and $Ni(NO_3)_2$ were prepared. These two solutions were added drop wise over a one-hour period to the stirred suspension (LP/surfactant/$H_2O$). The Mo/Ni molar ratio was 2/1. Following prolonged stirring for 3 hours at 60° C., the resulting black slurry was transferred into an autoclave and kept at 130° C. for 24 hours. The black precipitate was recovered from the mixture by centrifuging and washing with deionised water. The wet cake was dried in air at 100° C. followed by heat-treatment at 350° C. for 4 h under $N_2$ flow. The supported catalyst product produced by this microemulsion method is referred to herein as $NiMoS_2$-LP-HT.

Preparation of Unsupported $NiMoS_2$—Hydrothermal Method

The experimental procedure given above for the supported hydrothermally produced catalyst was followed to afford the unsupported catalyst with the exception of the steps relating to laponite. The unsupported catalyst product produced by this hydrothermal method is referred to herein as $NiMoS_2$-HT.

Results and Discussion

Characterisation of Laponite Supported $NiMoS_2$ Catalysts

FIG. 1 shows XRD patterns of $NiMoS_2$-LP-HT prepared by the hydrothermal method, $NiMoS_2$-LP-ME obtained from the microemulsion method of the invention, and of the laponite support alone. The laponite has a layered structure; interlayer basal spacing d(001) appeared at 7° 2theta on the XRD patterns. Absence of the basal peak (7° 2theta) indicated either: (1) complete exfoliation of laponite layers or (2) chemical decomposition of laponite by acid leaching during synthesis. It is apparent that laponite retained its layered structure during syntheses (both hydrothermal and microemulsion), as the XRD detected the basal (7° 2theta) peak in all three samples. The XRD pattern of NiMoS$_2$-LP-HT consisted of mainly laponite and MoS$_2$ phases. NiMoS$_2$-LP-ME generated weak XRD signals indicating the amorphous nature of samples.

Figure 2:
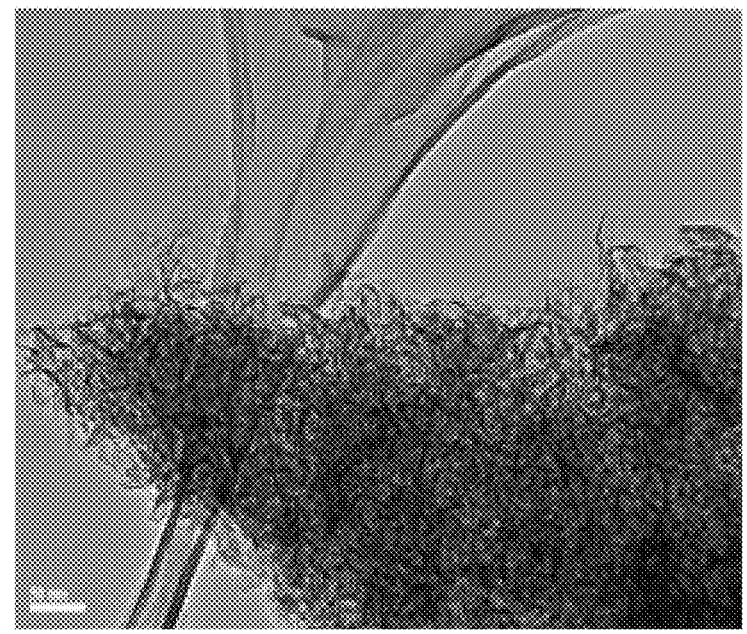
FIG. 2(a) to (c) is a series of TEM images of (a) laponite; (b) $NiMoS_2$-LP-HT; and (c) $NiMoS_2$-LP-ME.
Figure 2:
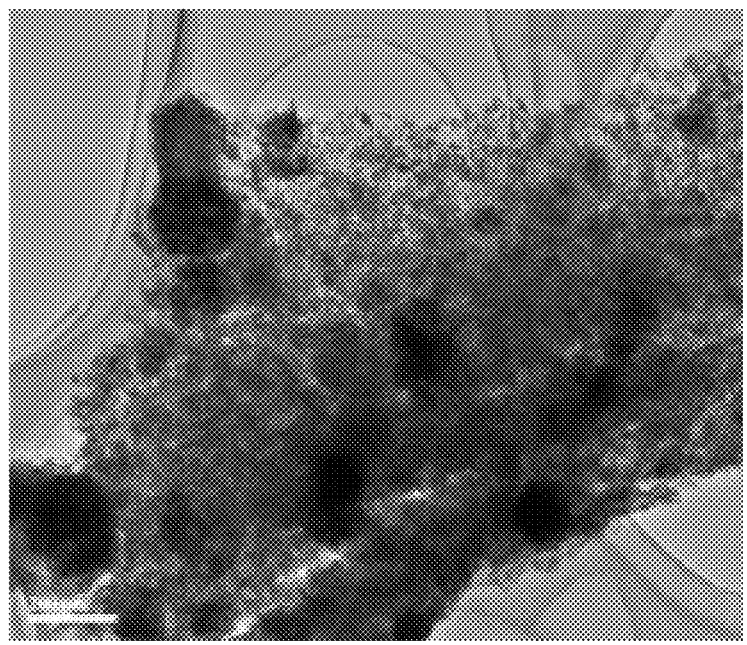
Figure 2:
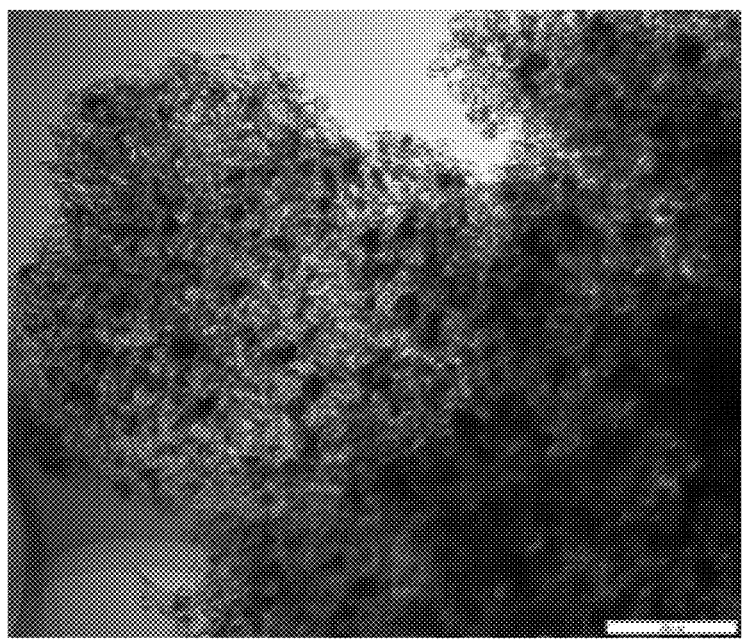

TEM images of the obtained catalyst samples are shown in FIG. 2. An image of commercial, bare laponite is provided (FIG. 2a) to clarify the laponite structure. NiMoS$_2$-LP-HT (FIG. 2b) and NiMoS$_2$-LP-ME (FIG. 2c) are also represented.

TEM images of NiMoS$_2$-LP-HT and NiMoS$_2$-LP-ME revealed dark catalyst particles distributed on the laponite support. The TEM image of NiMoS$_2$-LP-HT consisted of large aggregates (~200 nm), which were irregularly distributed across the laponite framework. In contrast, the TEM image of NiMoS$_2$-LP-ME demonstrated an ideal morphology for a catalyst, where fine particles (~20 nm) of active species were homogenously deposited on the support. Comparison of the TEM images of NiMoS$_2$-LP-HT and NiMoS$_2$-LP-ME catalysts revealed that the microemulsion method results in an ideal catalyst structure, featuring uniformly distributed NiMoS$_2$ particles on the laponite framework.

Figure 3:
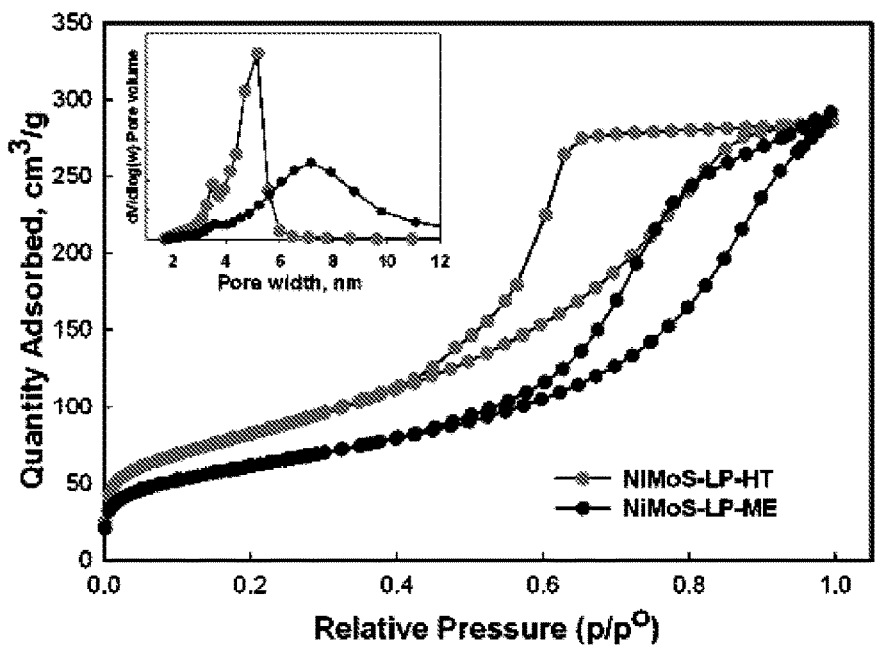
FIG. 3 is a graphical representation of the nitrogen physisorption isotherms and pore size distribution curves of $NiMoS_2$-LP-HT and $NiMoS_2$-LP-ME.

Nitrogen physisorption isotherms of the HT and ME supported catalysts corresponded to type IV isotherms, characteristic of mesoporous adsorbents, as shown in FIG. 3. BET surface areas of 300 m$^2$/g and 250 m$^2$/g were measured for the NiMoS$_2$-LP-ME and NiMoS$_2$-LP-HT catalysts, respectively. Pore size distribution curves of the two catalysts were compared and are also shown in FIG. 3. Bimodal pore size distribution was generated for both HT and ME catalysts, centred at 3.5 nm and 5.1 nm (NiMoS$_2$-LP-HT); 3.5 nm and 7.1 nm (NiMoS$_2$-LP-ME). Regardless of the different synthesis methods, both catalysts displayed an average pore size at 3.5 nm (BJH method). This pore size could arise from spaces between randomly orientated MoS$_2$ layers. Compared with the hydrothermal based sample, the microemulsion based samples had broader pore size distribution (PSD). The broad PSD was possibly caused by the non-ionic surfactant (Brij 30), used as a stabiliser of the microemulsions, having decomposed during heat-treatment leaving a porous structure and amorphous carbon residue.

Catalytic Performances of NiMoS$_2$-Laponite Catalysts

Catalytic performances of NiMoS$_2$-LP were studied at the laboratory scale in a fixed bed high-pressure reactor. By using the measured volumetric flow rate and the concentration of component i, the molar flow rate of component i was determined ($F_i$). The CO conversion was calculated using the molar flow rates of CO inlet and outlet stream of the reactor. An internal standard gas (nitrogen) was used to calculate the molar flow rates of CO in the outlet stream.

$$X_{CO} = \frac{F_{CO}^{in} - F_{CO}^{out}}{F_{CO}^{in}} \quad \text{Eq (1)}$$

The selectivity of a product was calculated using equation 2. Note that CO$_2$ content is included in the calculations of selectivity.

$$S_{Eth} = \frac{F_{eth}^{out}}{F_{CO}^{in} - F_{CO}^{out}} \quad \text{Eq (2)}$$

Figure 4:
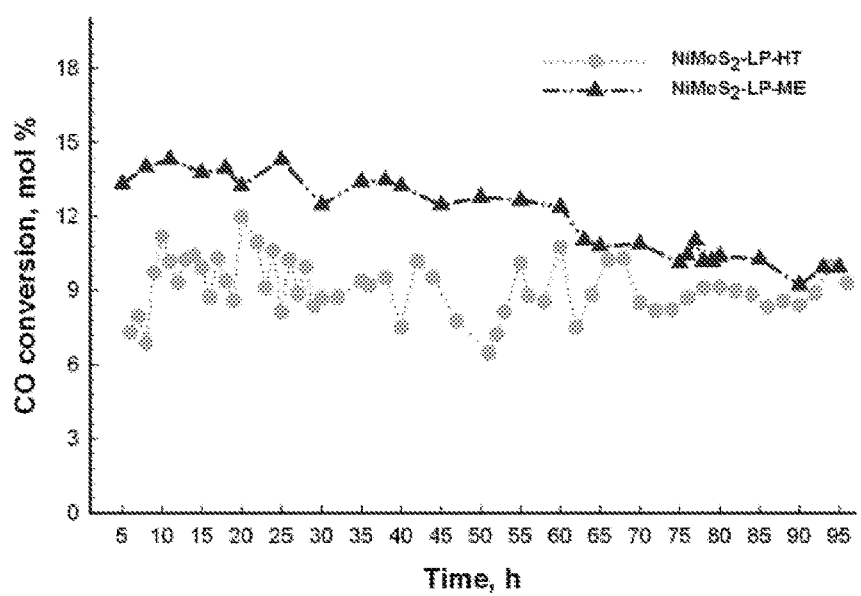
FIG. 4 is a graphical representation of the CO conversion of $NiMoS_2$-LP-HT and $NiMoS_2$-LP-ME catalysts.

To study CO conversion and the stability of the NiMoS$_2$LP, the CO hydrogenation reaction was conducted at 310° C., 60 bar and GHSV=1044 h$^{-1}$. Catalytic test results of the two catalysts are given in FIG. 4 and Table 1. NiMoS$_2$-LP-HT catalyst maintained stable CO conversion during the 95-hour reaction run while the NiMoS$_2$-LP-ME catalyst had advantageously high initial activity, with an eventual drop off with reaction time. Average CO conversion reached up to 14.5 mol % by NiMoS$_2$-LP-ME, whereas only 9.45 mol % of CO was converted into products by NiMoS$_2$-LP-HT. This represents a significant improvement over the hydrothermally produced catalyst.

The major outstream products of the NiMoS$_2$-LP-ME were methane and methanol with 34 mol % and 19 mol % selectivity, respectively.

TABLE 1

CO conversion and Selectivity of NiMoS$_2$-LP-HT and NiMoS$_2$-LP-ME catalysts [a].

| Catalysts | | NiMoS$_2$-LP-HT | NiMoS$_2$-LP-ME |
|---|---|---|---|
| X co [b] [mol %] | | 9.45 | 14.5 |
| S[c] [mol %] | HCs | 51.4 | 34.2 |
| | C$_1$—OH | 3.9 | 19.1 |
| | C$_2$—OH | 26.4 | 18.2 |
| | C$_3$—OH | 2.6 | 3.39 |
| | Other Oxy. | 0.3 | 1.71 |
| | Alcohol | 33.2 | 42.4 |
| [mol %] C$_2$—OH in total alcohol | | 79.5 | 43.2 |

Figure 5:
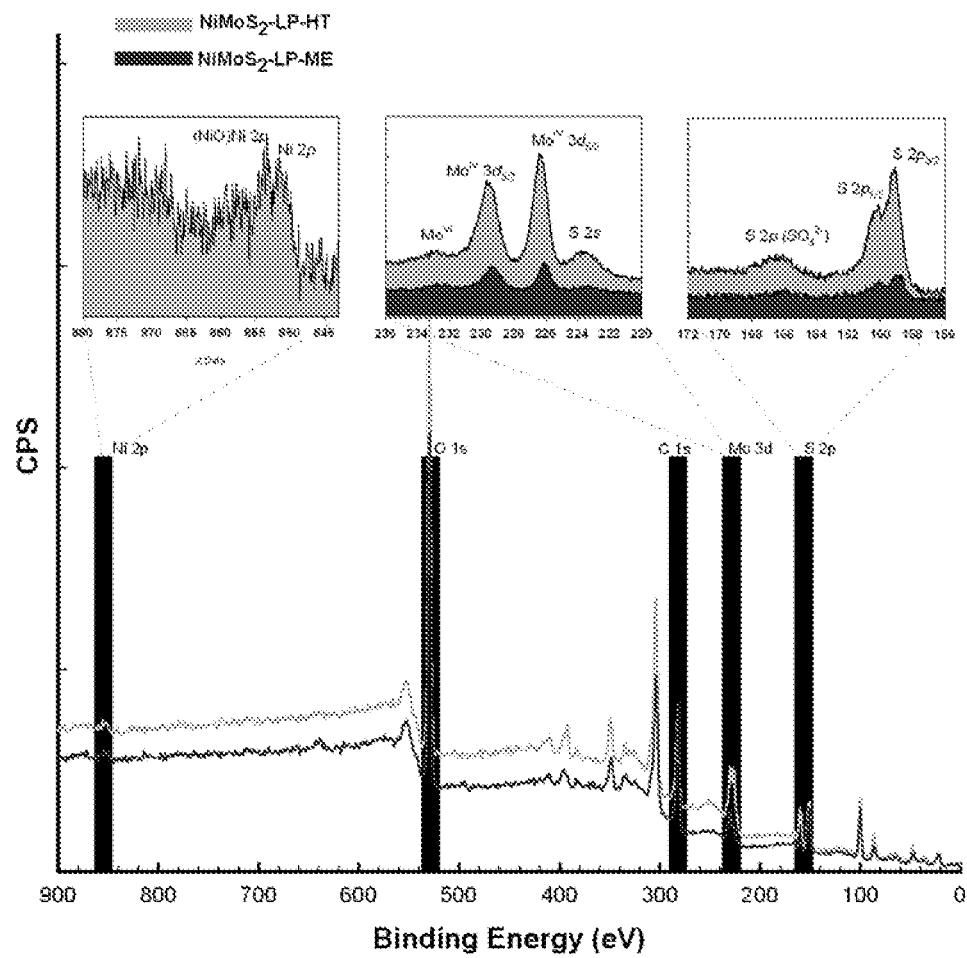
FIG. 5 is the XPS analysis results of $NiMoS_2$-LP-HT and $NiMoS_2$-LP-ME.

[a] Test conditions: P = 60 bar, GHSV = 1044 h$^{-1}$, H$_2$/CO = 2.
[b] CO conversion.
[c] C-based, selectivity of products CO$_2$ included To clarify the differences in catalytic performance of the two catalysts, XPS analysis was carried out (FIG. 5). The focus was to quantify surface elements and compare the quantity of surface elements in NiMoS$_2$-LP-HT and NiMoS$_2$-LP-ME catalysts. The XPS results were obtained from a survey (general) scan without further details on the oxidation state of the elements. As samples were exposed to air during XPS preparation, catalysts were not reduced before XPS analysis. Carbon and oxygen were the major elements on the surface of both catalysts, as is shown in Table 2. The atomic percentage of elements in NiMoS$_2$-LP-HT changed as: (1) molybdenum content remained unchanged, (2) sulphur content reduced from 5.48 at % to 4.37 at %, (3) nickel content equalled 1.31 at % before reaction and 0.82 at % after reaction on the surface.

TABLE 2

XPS analysis data of NiMoS$_2$-LP prepared by hydrothermal and microemulsion methods, analysed before and after reaction tests.

| Elements | NiMoS$_2$ LP-ME[F] at % | NiMoS$_2$ LP-ME[S] at % | NiMoS$_2$ LP-HT[F] at % | NiMoS$_2$ LP-HT[S] at % |
|---|---|---|---|---|
| Mo 3d | 1.91 | 1.7 | 2.74 | 2.8 |
| Ni 2p | 0.2 | 0.14 | 1.31 | 0.82 |
| S 2p | 1.05 | 0 | 5.48 | 4.37 |
| Mg 2s | 5.7 | 8.0 | 6.67 | 7.3 |
| Si 2p | 15.6 | 18.0 | 12.09 | 12.7 |

TABLE 2-continued

XPS analysis data of NiMoS$_2$-LP prepared by hydrothermal and microemulsion methods, analysed before and after reaction tests.

| Elements | NiMoS$_2$ LP-ME$^F$ at % | NiMoS$_2$ LP-ME$^S$ at % | NiMoS$_2$ LP-HT$^F$ at % | NiMoS$_2$ LP-HT$^S$ at % |
|---|---|---|---|---|
| C 1s | 37.3 | 32.68 | 25.12 | 23.1 |
| O 1s | 38.23 | 39.02 | 46.59 | 48.79 |

$^f$Fresh catalysts,
$^s$spent catalysts

Table 2 also shows XPS results of a sample prepared by the microemulsion method, where surface concentration of active species (Mo, Ni and S) was three times lower than the hydrothermal based samples (in fresh catalysts). Sulphur was not detected in spent NiMoS$_2$-LP-ME catalysts, whereas the surface concentration of nickel and molybdenum decreased after the reaction.

In the XPS of NiMoS$_2$-LP-ME catalysts, laponite species (magnesium, silicon, oxygen) dominated on the surface, which can result in a barrier between catalyst species (Mo Ni and S) and reactant molecules (CO and H$_2$). In the microemulsion method, NiMoS$_2$ particles were formed in a reverse emulsion (water in oil) system and their particle sizes were below 5 nm (some of them formed aggregates up to ~20 nm); laponite particles (d$_p$~30 nm) were dispersed in water without further size reduction. The different particle size likely caused the presence of most laponite particles on surface layers of catalyst and for this reason laponite particles generated stronger signals on XPS than the NiMoS$_2$ particles. This observation may well explain why laponite supported (NiMoS$_2$-LP-ME) catalysts did not deliver even higher catalytic activity beyond that already observed. This can potentially be addressed by varying the processing of the laponite prior to deposition of the catalyst. If the laponite particles were simply formed in-situ, together with the MoS$_2$-microemulsion, it is expected that the catalytic performance of NiMoS-LP-ME could be significantly improved.

The results discussed so far were based on textural and catalytic properties of laponite supported NiMoS$_2$ prepared by hydrothermal and microemulsion methods. In summary, the microemulsion method produced a NiMoS$_2$-LP catalyst with superior catalytic properties than the hydrothermal based catalysts. Comparison of TEM images revealed that the microemulsion method resulted in homogenously distributed NiMoS$_2$ particles on the laponite support. According to the XPS results, the surface of NiMoS$_2$-LP-ME was covered by laponite species (Mg, Si and O) and so a greater exposure to the active sites (Ni, Mo and S) would provide for an even higher CO conversion.

Catalytic Performances of Unsupported NiMoS$_2$ Catalysts

Figure 6:
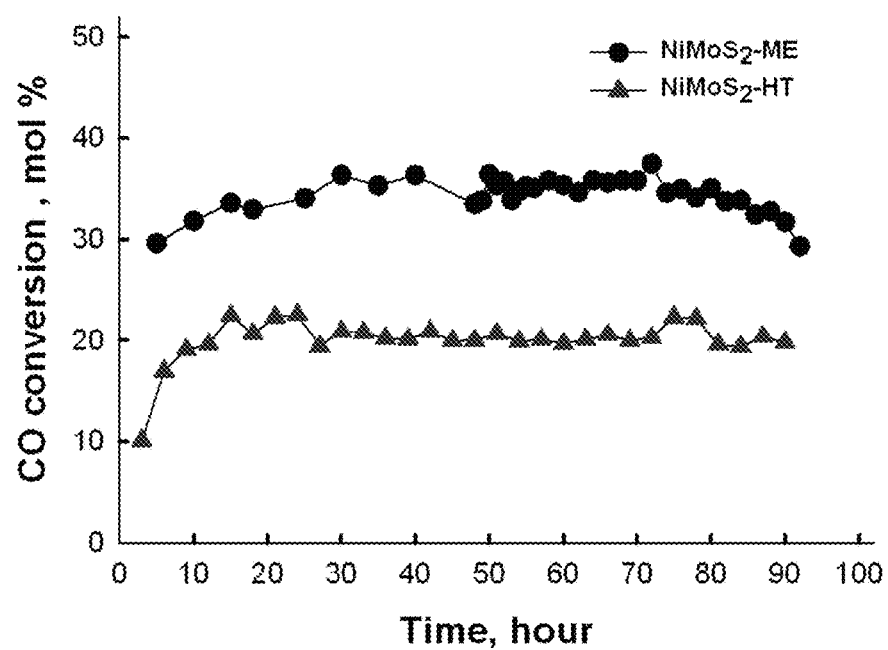
FIG. 6 is a graphical representation of CO conversion as a function of time on stream for $NiMoS_2$-HT and $NiMoS_2$-ME catalysts.

Unsupported NiMoS$_2$-HT and NiMoS$_2$-ME catalysts were also tested for the CO hydrogenation reaction under 60 bar at 310° C. FIG. 6 illustrates changes in CO conversion with time-on-stream. In the catalytic tests with NiMoS$_2$-HT, the CO conversion level remained stable during 92 hours of reaction. High catalytic activity was observed for the NiMoS$_2$-ME catalysts, resulting in an average CO conversion of 33 mol %. In contrast, the NiMoS$_2$-HT catalysts converted only 23 mol % of CO into products.

Product selectivity of the catalysts is given in Table 3. By using the NiMoS$_2$-HT catalyst, CO hydrogenation yielded mainly methane (30.2 mol %) and carbon dioxide (43.8 mol %), indicating a low selectivity nature towards alcohol formation. The ME-based catalysts resulted in a high percentage of alcohol (61 mol %) and significantly low amounts of methane (14.4 mol %) and carbon dioxide (23 mol %). As the same amount of NiMoS$_2$ active catalyst was loaded in the reactor for both cases, such a significant difference in catalytic properties was unexpected, especially in product selectivity.

TABLE 3

CO conversion and Selectivity of NiMoS$_2$-HT and NiMoS$_2$-ME catalysts $^a$.

| Catalysts | | NiMoS$_2$-HT | NiMoS$_2$-ME |
|---|---|---|---|
| X co $^b$ [mol %] | | 23 | 33 |
| S$^c$ [mol %] | HCs | 30.2 | 14.4 |
| | C$_1$—OH | 5.25 | 28.1 |
| | C$_2$—OH | 8.7 | 26.8 |
| | C$_3$—OH | 0.75 | 4.27 |
| | Other Oxy. | 0.28 | 1.83 |
| | Alcohol | 15 | 61 |
| [mol %] C$_2$—OH in total alcohol | | 58 | 44 |

Figure 7:
FIG. 7(a and b) is a series of TEM images of unsupported $NiMoS_2$-ME (a) and (b) $NiMoS_2$-HT catalysts.
Figure 7:
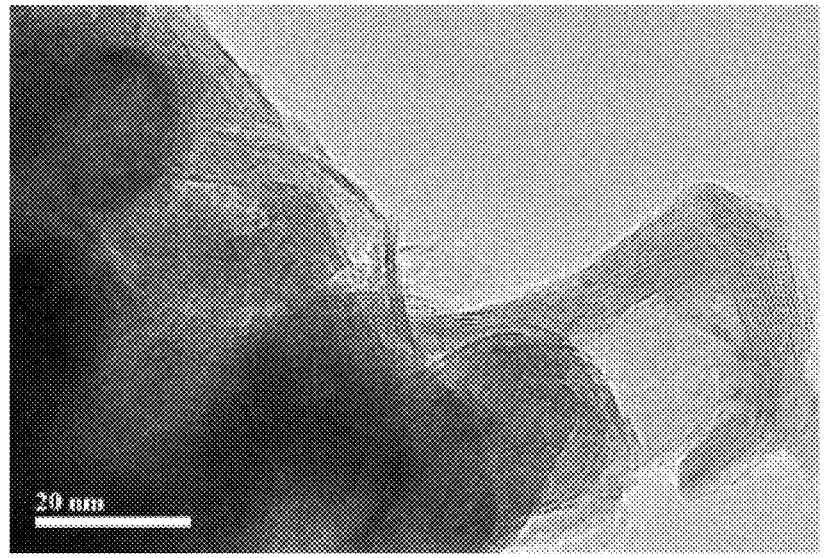

$^a$ Test conditions: P = 60 bar, GHSV = 1044 h$^{-1}$, H$_2$/CO = 2.
$^b$ CO conversion.
$^c$C-based, selectivity of products CO$_2$ included To clarify the major differences between the unsupported hydrothermal and microemulsion based catalysts, TEM and SEM observations were carried out. As shown in the images of FIG. 7 (TEM) and FIG. 8 (SEM) the morphology of the NiMoS$_2$ was highly dependent on the synthesis method. TEM images of the NiMoS$_2$-ME catalyst consisted of highly disordered MoS$_2$ layers; in some areas up to three layers were detected. In contrast stacks of MoS$_2$ containing 6-7 sulphide layers and well-crystallised sulphide slabs were observed from the NiMoS$_2$-HT catalyst. These TEM images indicate that the microemulsion method advantageously results in highly disordered and short sulphide layers (~10 nm), whereas the hydrothermal synthesis produced continuous and well-crystallised multi-layers of MoS$_2$. SEM images of NiMoS$_2$-ME catalyst contained small and plate shaped particles, whereas NiMoS$_2$-HT catalyst consisted of large aggregates.

Figure 8:
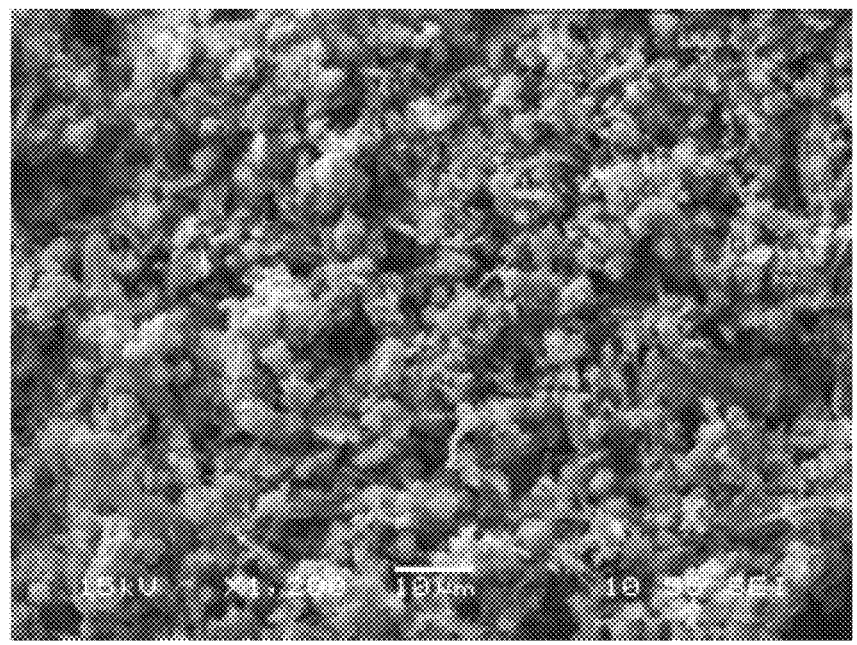
FIG. 8(a and b)) is a series of SEM images of unsupported $NiMoS_2$-ME (a) and (b) $NiMoS_2$-HT catalysts.
Figure 8:
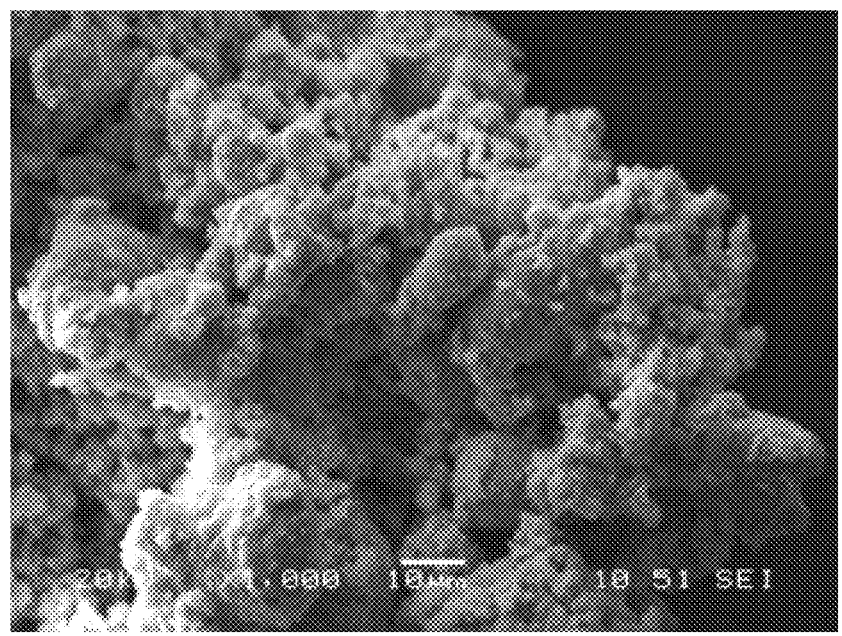

Referring to FIG. 7 (TEM) and FIG. 8 (SEM), it is obvious that the NiMoS$_2$-HT catalyst forms large aggregates, whereas the NiMoS$_2$-HT catalyst did not undergo such aggregation. The lack of these large aggregations increases the surface area of the catalyst and results in higher catalytic activity.

Using nitrogen physisorption, a BET surface area of 120 m$^2$/g and pore volume of 0.45 ml was measured for the NiMoS$_2$-ME catalysts. A BET surface area of only 6 m$^2$/g was found for the NiMoS$_2$-HT catalysts. TEM and SEM images of the hydrothermal based catalysts showed highly ordered sulphide slabs, in agreement with the small BET surface area and pore volume found for the sample. The large BET surface area found for the NiMoS$_2$-ME catalyst was associated with the highly disordered sulphide layers and carbon residue (26 wt. %) and the latter may act as a useful dispersant for particles by creating a porous network.

Surface Analysis Characterisation of Unsupported NiMoS$_2$ Catalysts

Major differences were found in XPS analysis data of HT and ME based catalysts. XPS analysis was performed for fresh and spent catalysts and XPS spectra and one example of the curve fittings are presented in FIGS. 9A and 9B.

An XPS survey scan of the fresh NiMoS$_2$-ME catalyst generated strong signals of oxygen and carbon, and weak signals of Mo 3d and S 2p (Table 4). The NiMoS$_2$-ME catalyst yielded a binding energy of 229.3 eV and 232.7 eV which is characteristic of Mo 3d$_{5/2}$ (Mo$^{4+}$) and Mo 3d$_{5/2}$ (Mo$^{6+}$), respectively. An XPS spectrum of the sulphur region revealed two S 2p$_{3/2}$ doublets with binding energies of 162 eV and 164 eV which is indicative of the presence of S$^{2-}$ ions and S$_2^{2-}$ groups. Correlating the XPS spectra of sulphur (S 2p), molybdenum (Mo 3d) and an atomic ratio of S/Mo: 2, a binding energy of 229.3 eV was assigned to MoS$_2$. This does not exclude the presence of MoO$_2$.

TABLE 4

XPS analysis data and ICP results of unsupported NiMoS$_2$ prepared by hydrothermal and microemulsion methods, analysed before and after reaction tests.

|  |  | NiMoS$_2$ ME$^F$ | NiMoS$_2$ ME$^S$ | NiMoS$_2$ HT$^F$ | NiMoS$_2$ HT$^S$ |
|---|---|---|---|---|---|
| XPS data at % | Mo 3d | 5.16 | 6.89 | 7.98 | 8.59 |
|  | S 2p | 10.16 | 2.31 | 15.13 | 17.16 |
|  | Ni 2p | 0 | 1.19 | 1.76 | 1.82 |
|  | C 1s | 67.14 | 61.9 | 39.45 | 33.54 |
|  | O 1s | 17.56 | 27.72 | 35.03 | 38.89 |
| Surface composition from XPS |  | Ni$_0$MoS$_{1.96}$ | Ni$_{0.17}$MoS$_{0.33}$ | Ni$_{0.22}$MoS$_{1.89}$ | Ni$_{0.21}$MoS$_{1.99}$ |
| Elemental composition from ICP |  | Ni$_{0.41}$MoS$_{1.93}$ | Ni$_{0.48}$MoS$_{0.75}$ | Ni$_{0.43}$MoS$_{2.11}$ | Ni$_{0.47}$MoS$_{1.77}$ |

$^F$Fresh catalysts,
$^S$spent catalysts

The XPS revealed a small peak at 229.3 eV, characteristic of Mo 3d$_{5/2}$(Mo$^{4+}$), in Mo 3d regions of spent NiMoS$_2$-ME catalyst. In addition, the spectrum displayed some contribution from Mo$^{5+}$ with 230.9 eV and a large peak corresponding to Mo 3d$_{5/2}$ (Mo$^{6+}$) at 232.8 eV. Measurement in the S 2p region detected sulphur with a significantly low concentration (2.3 at %), yielding one S 2p$_{3/2}$ doublet with a binding energy of 162.2 eV. Surface atomic ratio of S/Mo corresponded to 0.33. An increase of Mo 3d$_{5/2}$ (Mo$^{6+}$) contribution and low sulphur content indicated that a significant amount of sulphur was lost during the reaction that led to the oxidation of Mo$^{4+}$species to Mo(V) and Mo (VI) oxides.

Figure 9A:
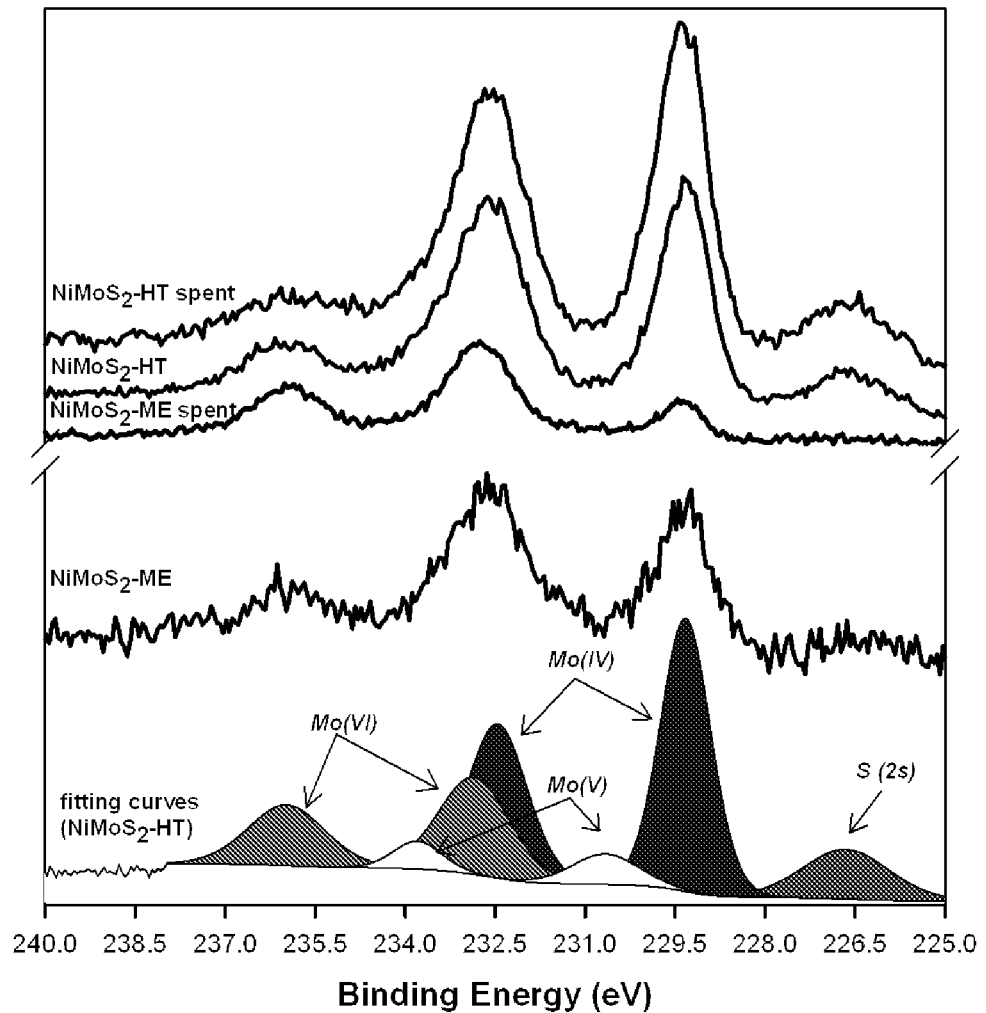
FIG. 9A is a graphical representation of XPS analysis results of $NiMoS_2$-HT and $NiMoS_2$-ME, fresh and spent catalysts (High-resolution scan in Mo 3d regions)
Figure 9B:
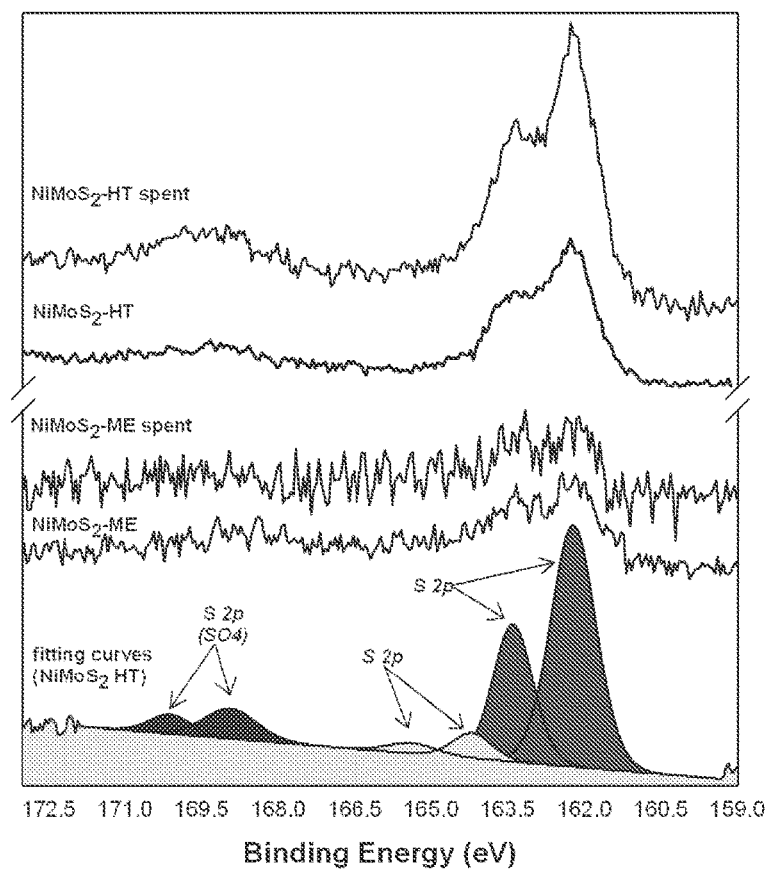
FIG. 9B is a graphical representation of XPS analysis results of $NiMoS_2$-HT and $NiMoS_2$-ME, fresh and spent catalysts (High-resolution scan in S 2p regions)

FIGS. 9A and B also illustrate XPS spectra of NiMoS$_2$-HT catalysts. A minor difference was observed in XPS data of fresh and spent NiMoS$_2$-HT catalysts, especially in the concentration of surface elements and Mo 3d and S 2p line positions (Table 4).

Fresh NiMoS$_2$-HT catalysts in the Mo 3d regions contain three molybdenum oxidation states: 1) Mo 3d$_{5/2}$ (Mo$^{4+}$) at 229.3 eV; 2) Mo 3d$_{5/2}$ (Mo$^{5+}$) at 230.6 eV; and 3) Mo 3d$_{5/2}$ (Mo$^{6+}$) 232.8 eV. These line positions remained unchanged in spent NiMoS$_2$-HT catalysts. Regarding the S 2p regions, a weak and broad shoulder at a position of 169 eV, consistent with S 2p$_{3/2}$ for SO$_4$ groups, existed together with two S 2p$_{3/2}$ doublets at 162.2 and 164.5 eV, respectively. Importantly, this indicates that, compared with the NiMoS$_2$-ME catalyst, the NiMoS$_2$-HT catalyst retained its surface sulphur content during catalytic testing giving surface atomic ratios of 2 for S/Mo for both NiMoS$_2$-HT fresh and spent catalysts.

Total concentration of (Mo, Ni and S) elements in fresh and spent catalysts was also analysed by ICP and results are seen in Table 4. ICP analysis results revealed that the NiMoS$_2$-ME catalyst lost a significant amount of sulphur during the reaction which concurs with the XPS analysis. The chemical composition of NiMoS$_2$-ME catalyst changed from Ni$_{0.41}$MoS$_{1.93}$ to Ni$_{0.48}$MoS$_{0.75}$ after the reaction. In the NiMoS$_2$-HT catalyst, the composition changed as Ni$_{0.43}$MoS$_{2.11}$ (fresh) and Ni$_{0.47}$MoS$_{1.77}$ (spent).

Correlation Between Sulphur Loss and Catalyst Activity

It is apparent that during the exposure of MoS$_2$ catalyst into the syngas feed a loss of sulphur was observed for the microemulsion-derived catalysts. It is apparent that sulphur, located at the edges of sulphide layers, can react with hydrogen leaving coordinatively unsaturated Molybdenum ions and anionic vacancies. In hydrotreating MoS$_2$ catalysts, the adsorption of molecules such as O$_2$, CO, N$_2$ and NH$_3$ has been shown to mainly take place on the anionic vacancy sites of sulphide catalysts. A correlation between the active sites and improved catalytic activity was reported in these catalysts. For other sulphide catalysts (NiWS) used in hydrocracking, hydrodesulphurisation, and hydrogenation reactions, the anionic vacancies (sulphur deficient metal sites) were the catalytic active centres but could be blocked in the presence of H$_2$S. Without wishing to be bound by any particular theory, the present inventors postulate that a similar phenomenon could take place with the MoS$_2$ catalyst during the alcohol synthesis reaction. The catalyst prepared by ME methods had a significantly higher selectivity towards syngas conversion to alcohol than hydrocarbons. Based on the XPS results, which detected a substantial decrease in sulphur content after the reaction (Ni$_0$MOS$_{1.96}$ fresh; Ni$_{0.17}$MoS$_{0.33}$ spent) and catalytic tests, it is interesting to correlate the high alcohol selectivity with the presence of coordinatively unsaturated Molybdenum sites. Assuming that any alcohol precursors originate from the coordinatively unsaturated Molybdenum sites a postulated mechanism for alcohol formation can be drawn as shown in FIG. 10.

Figure 10:
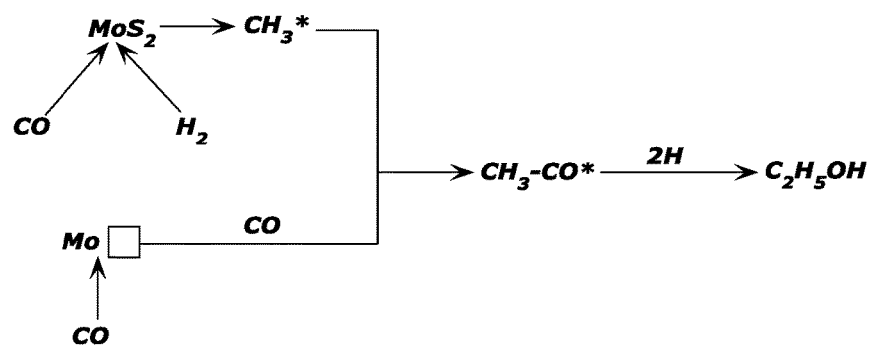
FIG. 10 is a reaction mechanism for formation of ethanol via adsorption of CO molecules in sulphur vacancy molybdenum sites.

The mechanism shown in FIG. 10 supports the reaction path whereby non-dissociated CO molecules are absorbed into CH$_3$-methyl species. As the NiMoS$_2$-ME catalysts contain layered sulphide (up to 2 layers), sulphur, located at other than surface planes and edge sites, most likely remains in the structure and contributes to the formation of CH$_3$-metyl species through the CO and H$_2$ dissociation occurring in charge neutral molybdenum sites/fully sulphurised molybdenum sites. Moreover, dissociation of hydrogen on sulphur deficient sites cannot be ruled out.

Based on the observed data it can be concluded that the microemulsion method of the present invention produces highly active $NiMoS_2$ catalysts with higher ethanol selectivity than the hydrothermal method. The microemulsion-based catalyst feature disordered sulphide structures, sulphur vacancies and large BET surface area. The results presented herein emphasize that a highly disordered sulphide structure, in combination with coordinatively unsaturated Mo sites, is the optimal basis for the synthesis of alcohols, particularly ethanol, from syngas.

The method of the present invention allows for the synthesis of highly active catalysts for use in ethanol synthesis from syngas. $NiMoS_2$ catalysts prepared by the microemulsion method demonstrated larger BET surface areas (120 m$^2$/g), higher CO hydrogenation activity (33 mol % CO conversion) and higher selectivity to alcohol (61 mol %) compared to the hydrothermal based $NiMoS_2$ catalysts. XPS and ICP results of spent catalysts revealed a significant loss of sulphur, especially in $NiMoS_2$-ME catalyst. The high catalytic activity of the $NiMoS_2$-ME catalyst is associated with its highly disordered sulphide layers, which are readily reduced under syngas atmosphere by releasing sulphur from its structure. Release of sulphur from the catalyst structures creates anionic vacancies that promote the formation of alcohol via $CH_3$-methyl and CO coupling.

The Syngas Conversion and Alcohol Selectivity of Potassium promoted $NiMoS_2$

Catalyst $NiMoS_2$ was promoted with potassium using the microemulsion method. Previous work has highlighted the importance of potassium in the formation of ethanol. However, the role of potassium is unclear; it has been postulated that potassium increases the basicity of the catalyst, or potassium addition may be related to a change in molybdenum oxidation state (IV). Previous studies have introduced a potassium source to the $NiMoS_2$ by physical mixing. The inventors introduced an aqueous potassium source ($CH_3COOK$) to the $NiMoS_2$ water/oil emulsions and no additional heat-treatment was applied except reduction under hydrogen atmosphere.

Figure 11:
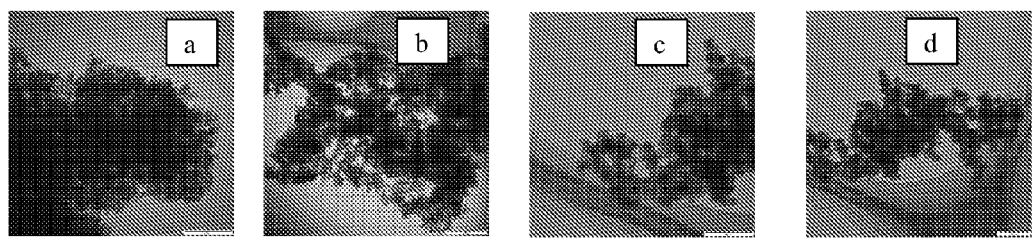
FIG. 11a-d are TEM images of K-$NiMoS_2$ with a) 0 wt % K, b) 10 wt %, c) 20 wt % and d) 30 wt %.

FIG. 11 shows TEM images of K-$NiMoS_2$ with varying amounts of potassium; a) 0 wt % K, b) 10 wt %, c) 20 wt % and d) 30 wt %. The catalyst particles structure retained its original structure upon addition of potassium and no major changes in the structure are observed in samples with high potassium loadings.

Figure 12:
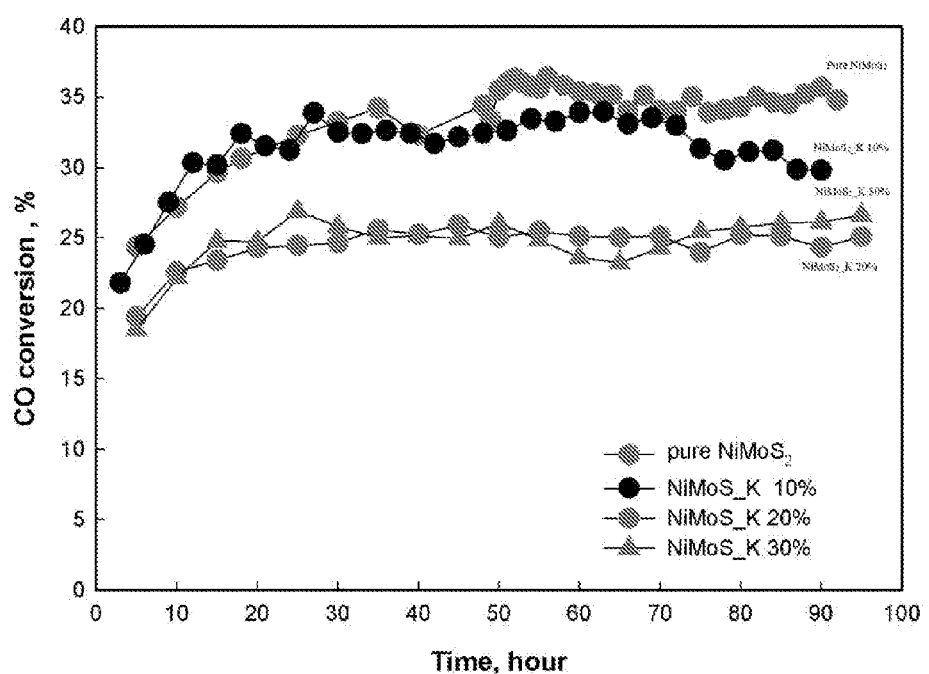
FIG. 12 is a graphical representation of CO conversion with reaction time for potassium promoted catalyst samples K-$NiMoS_2$.

FIG. 12 shows a graphical representation of the change in CO conversion with reaction time for the different amounts of potassium promoted catalyst samples K-$NiMoS_2$. The increase in potassium loading subsequently lowered the CO conversion from (10K-NiMoS) 33 mol% to 25 mol % (30K-$NiMoS_2$) CO conversion.

Figure 13:
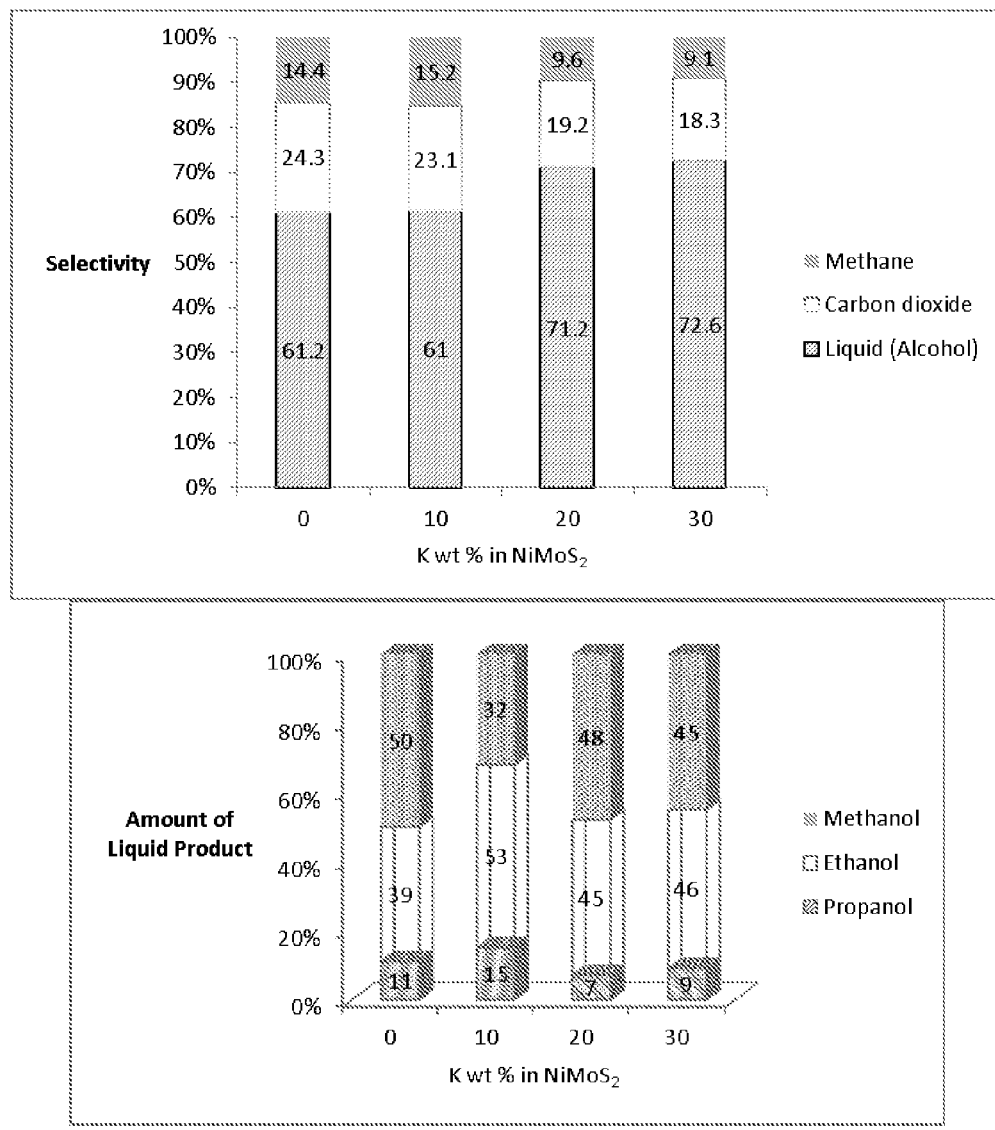
FIG. 13 is a graphical representation of the selectivity of product obtained by using potassium promoted catalyst samples K-$NiMoS_2$.

FIG. 13 shows the selectivity of the products obtained using potassium promoted catalyst samples K-$NiMoS_2$. It can be seen that the formation of methane and carbon dioxide (by-products) decrease with the increase of potassium loading. It can be seen clearly in FIG. 13b that the selectivity of alcohol in liquid product effected by the potassium loading. The formation of ethanol is favoured in the catalyst sample with 10 wt % potassium loading (10K-$NiMoS_2$).

It has not been previously appreciated that the morphology observed in catalysts synthesised by the present method would be so effective in the conversion of syngas to alcohol. Indeed, it has not been appreciated that a microemulsion-based synthesis approach would provide for a Molybdenum sulphide catalyst with such a distinctive morphology. The results presented herein have demonstrated the strong link between the particular morphology generated in the ME process and the effectiveness and selectivity of syngas to alcohol conversion.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this patent specification is intended to embrace all alternatives, modifications and variations of the present invention that have been discussed herein, and other embodiments that fall within the spirit and scope of the above described invention.

In the claims which follow and in the preceding description of the invention, except where the context clearly requires otherwise due to express language or necessary implication, the word "comprise", or variations thereof including "comprises" or "comprising", is used in an inclusive sense, that is, to specify the presence of the stated integers but without precluding the presence or addition of further integers in one or more embodiments of the invention.

The invention claimed is:

1. A method of producing a solid catalyst including the steps of:
    (a) providing a non-polar solvent;
    (b) forming MoS2 within the non-polar solvent by combining, in aqueous solution added to the non-polar solvent, a sulfide compound and a molybdenum compound; and
    (c) adding a salt of a transition metal selected from the group consisting of nickel, cobalt, and iron to the non-polar solvent;
    to thereby form a water-in-oil microemulsion and produce the solid catalyst.

2. The method of claim 1, wherein the step of forming the MoS2 within the non-polar solvent is achieved by: (i) adding an aqueous solution of the sulfide to the non-polar solvent, and (ii) adding an aqueous solution of the molybdenum compound to the non-polar solvent.

3. The method of claim 1, wherein the non-polar solvent is selected from the group consisting of oils, aliphatic hydrocarbons, saturated cyclic hydrocarbons, aromatic hydrocarbons, and halogenated hydrocarbons.

4. The method of claim 1, wherein the aqueous solution of the molybdenum compound is added to the non-polar solvent containing the aqueous solution of the sulfide.

5. The method of claim 1, wherein the sulfide compound is any at least water-soluble sulfide source.

6. The method of claim 1, wherein the molybdenum compound is any molybdenum containing compound that is water soluble.

7. The method of claim 6, wherein the molybdenum compound is selected from the group consisting of ammonium molydates, molybdenum oxides and water soluble alkali metal, and alkaline earth metal molybdates.

8. The method of claim 1, wherein the salt of the transition metal is selected from the group consisting of a nitrate, acetate, halide, sulfate, sulfide, oxalate, and carbonate salt.

9. The method of claim 1, wherein the salt of the transition metal is added to the non-polar solvent as an aqueous solution.

10. The method of claim 1, wherein the non-polar solvent comprises a surfactant.

11. The method of claim 1, further including the step of adding a dopant.

12. The method of claim 1, further including the step of adding a promoter agent.

13. The method of claim 12, wherein the promoter agent is added before or with the addition of the transition metal salt.

14. The method of claim 1, further including the step of adding a support to the non-polar solvent.

15. The method of claim 14, wherein the support is clay.

16. The method of claim 15, wherein the clay is selected from the group consisting of laponite, bentonite, montmorillonite, hectorite, and beidellite.

* * * * *